United States Patent [19]

Hsiao

[11] Patent Number: 4,874,613
[45] Date of Patent: Oct. 17, 1989

[54] TASTE CONCEALING PHARMACEUTICAL DOSAGE UNIT

[75] Inventor: Charles Hsiao, Copper City, Fla.

[73] Assignee: Baker Cummins Pharmaceuticals, Inc., Miami, Fla.

[21] Appl. No.: 253,704

[22] Filed: Oct. 5, 1988

Related U.S. Application Data

[63] Continuation-in-part of Ser. No. 23,035, Mar. 6, 1987, abandoned.

[51] Int. Cl.$^4$ .................................................. A61K 9/54
[52] U.S. Cl. .................................... 424/458; 424/451; 424/456; 424/459; 424/461; 424/462; 424/490; 424/494; 424/497
[58] Field of Search ............... 424/456, 451, 459, 461, 424/462, 458, 490, 494, 497; 206/634, 528, 532, 540

[56] References Cited

U.S. PATENT DOCUMENTS

| | | | |
|---|---|---|---|
| 4,001,399 | 1/1977 | Osono et al. | 424/123 |
| 4,021,543 | 5/1977 | McKay | 424/180 |
| 4,423,027 | 12/1983 | Simon et al. | 424/16 |
| 4,486,412 | 12/1984 | Shah et al. | 424/156 |
| 4,508,702 | 4/1985 | Hsiao | 424/19 |
| 4,513,019 | 4/1985 | Brancq et al. | 427/3 |
| 4,600,708 | 7/1986 | Reuter et al. | 514/78 |

FOREIGN PATENT DOCUMENTS

| | | |
|---|---|---|
| 0036345 | 9/1981 | European Pat. Off. . |
| 0050191 | 4/1982 | European Pat. Off. . |
| 0069097 | 1/1983 | European Pat. Off. . |
| 0119480 | 9/1984 | European Pat. Off. . |
| 0177368 | 4/1986 | European Pat. Off. . |
| 0013719 | 1/1985 | Japan . |
| 0199365 | 10/1985 | Japan . |
| 2077693 | 12/1981 | United Kingdom . |
| 2081092 | 2/1982 | United Kingdom . |
| 2122490 | 1/1984 | United Kingdom . |

OTHER PUBLICATIONS

Chemical Abstract, 104:50087V, 1985.
Chemical Abstract, 97060907p, 1981.
Chemical Abstract, 103:129052t, 1983.
Chemical Abstract, 102:50776c, 1984.
Chemical Abstract, 96:40911m, 1980.
Chemical Abstract, 105:30046y, 1984.
Chemical Abstract, 90:149483a, 1978.
Chemical Abstract 90:109891a, 1978.
Chemical Abstract, 90:109892b, 1978.
Chemical Abstract, 93:107863f, 1977.
Search Report Prepared for the Inventor by an Independent Searcher.

*Primary Examiner*—Thurman K. Page
*Attorney, Agent, or Firm*—Kirschstein, Ottinger, Israel & Schiffmiller

[57] ABSTRACT

A pharmaceutical dosage unit suitable for masking the unpleasant taste of orally administered pharmaceutical agents and which facilitates swallowing comprises a plurality of subdosage units disposed within a container. Each subdosage unit is a pellet with an inner core coated with an active pharmaceutical agent, a first layer surrounding the core comprising a biologically inert excipient or filler, and a second layer surrounding the first layer comprising a mixture of a cationic copolymeric acrylate resin and a basic compound. The container of the dosage unit may be orally ingestible in itself, such as an openable gelatin capsule, or may be a frangible packet which must be opened in order to orally administer the subdosage pellets to a patient.

15 Claims, No Drawings

TASTE CONCEALING PHARMACEUTICAL DOSAGE UNIT

CROSS-REFERENCE TO RELATED APPLICATION

This application is a continuation-in-part of co-pending application Ser. No. 07/23,035 filed Mar. 6, 1987 now abandoned.

BACKGROUND OF THE INVENTION

Orally administered pharmaceutical preparations are traditionally presented in the form of tablets, capsules, caplets, and the like, whether in ordinarily or sustained-release form. Such oral dosage units may, however, be difficult for certain patients to swallow because of their size and shape. In addition, the coatings conventionally used on traditional oral dosage units may themselves have an unpleasant taste or texture or may dissolve quickly upon contact with saliva in the mouth, causing the frequently bitter or unpleasant taste of the active pharmaceutical ingredient contained in the dosage unit to be sensed. Such factors may act as serious deterrents to the taking of medication by certain individuals, particularly children, mentally incapacitated patients and, in the case of veterinary preparations, small animals.

Various modified oral dosage units have been proposed in the prior art in an attempt to overcome the taste and swallowing problems associated with conventional dosage forms.

For example, in U.S. Pat. No. 3,922,379, orally active erythromycin derivatives were microencapsulated by suspending particles of said derivatives in water containing a water-soluble albumin and then stirring such suspension into a mixture of a liquid alkane and a non-ionic surfactant. The resultant microcapsules reportedly were effective in concealing the notoriously bitter taste of the erythromycin.

U.S. Pat. No. 3,919,436 discloses the use of a polymer containing as an essential component a substituted acrylamide as a coating substance for pharmaceutical tablets and granules.

U.S. Pat. No. 4,001,390 discloses a more complex coating system for solid dosage forms comprising an undercoat of a polymeric substance, a secondary coat consisting of a polymeric substance and a pigment, and a third or finish coat composed substantially of a polymeric substance.

The foregoing techniques for providing taste concealing coatings for oral dosage units are relatively complex and expensive for broad commercial use and may inhibit rapid dissolution (or smooth sustained release, in the case of sustained-release dosage forms), delaying the effective onset of the desired pharmaceutical activity. Moreover, the aforementioned prior art coating methods and substances do not significantly facilitate the swallowing of the oral dosage units and, thus, provide little advantage to patients who have difficulty in swallowing such medications.

In my recently issued U.S. Pat. No. 4,708,867, I disclosed a dosage form of the steroids prednisone and prednisolone which comprised an aggregate of minipellets contained within an ingestible capsule or other openable container. Each of the minipellets comprised the active drug coated on a nonpareil seed and surrounded by a layer of a copolymer of dimethylaminoethyl- and methylmethacrylate. Said minipellets were effective in concealing the unpleasant taste of the steroids and could be swallowed directly from the opened container, avoiding the problems associated with the swallowing of larger dosage units. Even these minipellets, however, suffer from certain drawbacks, including the difficulty in their manufacture resulting from the tackiness of the polymer coating.

SUMMARY OF THE INVENTION

1. Objects of the Invention

It is a general object of the present invention to provide a novel dosage form for oral administration of active pharmaceutical agents which avoids the aforementioned drawbacks of the prior art in terms of concealing the taste of the active ingredients while facilitating swallowing and providing a pharmaceutically acceptable release rate of active ingredient within the digestive tract.

It is another object of the present invention to provide an oral dosage unit as aforementioned which may be ingested in its entirety or opened to permit the swallowing of a plurality of subdosage units contained therein.

A further object of the present invention is to provide a dosage unit that is easily and inexpensively manufactured, and which contains subdosage units that are nontacky and provide excellent and long-lasting taste concealing properties.

2. Brief Description of the Invention

In keeping with these objects, and others which will become apparent hereinafter, the present invention resides, briefly stated, in a pharmaceutical dosage unit comprising a plurality of subdosage units disposed within a container, each of said subdosage units being a pellet having an average diameter not greater than about 1 mm and including: (a) an inner core coated with an orally active pharmaceutical agent; (b) a first or inner layer surrounding said core comprising a biologically inert excipient or filler; and (c) a second layer surrounding said first layer comprising a mixture of from about 10% to about 90% by weight of a cationic copolymer acrylate resin, and from about 10% to about 90% by weight of a basic compound selected from the group consisting of calcium carbonate, aluminum hydroxide and magnesium carbonate.

The first or inner layer of biologically inert filler provides a taste concealing barrier for the active ingredient. The basic compound admixed with the polymeric material in the outer layer provides a non-tacky consistency for said layer and helps promote dissolution of the subdosage unit in the acidic gastric juices.

DETAILED DESCRIPTION OF THE PREFERRED EMBODIMENTS

The dosage unit of the present invention comprises a plurality of pellet or minipellet-like subdosage units within a container. The container may be orally ingestible in itself, such as an openable gelatin capsule, or may comprise a frangible packet such as described in detail in my co-pending application Ser. No. 07/227,904. In the latter case, of course, the packet or container must be broken open and the subdosage units or pellets administered directly into the patient's mouth or into a liquid or onto a solid or semi-solid food which is subsequently ingested by the patient. Even in a case where the container consists of an ingestible capsule or the like, the container may be opened and the pellets contained therein ingested for ease of swallowing.

Each subdosage unit comprises an inner core consisting of particles of a biologically acceptable salt, a sugar, or calcium phosphate. A preferred core material is a sugar particle known as a nonpareil seed. The core is coated with a layer of the desired orally active pharmaceutical agent, preferably after the core is treated with a binding agent, e.g., polyvinylpyrrolidone, methylcellulose, and pharmaceutically suitable gums.

After the pellet core is coated with the active ingredient, it is surrounded by a first or inner layer of a biologically inert filler or excipient such as a biologically inert clay (e.g., kaolin clay) or a water-soluble polymer (e.g., methylcellulose). This layer of inert filler serves the primary purpose of masking the taste of the active ingredient while not interfering with its release from the pellets into the digestive system.

The second or outer layer which surrounds the inner layer of inert filler comprises a mixture of from about 10% to about 90% by weight of a cationic copolymer acrylate resin, and from about 10% to about 90% by weight of a basic compound selected from the group consisting of calcium carbonate, aluminum hydroxide and magnesium carbonate. Preferred weight concentrations for this mixture are from about 40% to about 70% of the copolymer, and from about 30% to about 60% of the basic compound.

As a cationic copolymeric acrylate resin, there is contemplated any resin based on methacrylate and neutral methacrylic acid ester copolymers. An example of such a cationic copolymeric acrylate resin is Eudragit E (Pharma International).

The subdosage units or pellets should have an average diameter no greater than 1 mm. Each dosage unit, may contain from about 50 to about 1000 subdosage units, preferably from about 200 to about 1000 subdosage units, although the number of pellets in each dosage unit may exceed 1000 depending on the desired dosage strength of the unit. It is also preferred that the aggregate quantity of the pharmaceutically active agent contained in all of the subdosage units within one dosage unit comprise a pharmaceutically effective dosage amount of said active agent, so that if all of the subdosage units or pellets within a dosage unit are ingested by a patient, the patient will have received a suitable dose of the subject medication.

Any orally active pharmaceutical ingredient may be incorporated into novel dosage units according to the present invention. Examples of such pharmaceutically active agents include chlorpheniramine [gamma-(4-chlorophenyl)-N,N-dimethyl-2-pyridinepropanamine-1,2-ethylenedicarboxylic acid], disclosed in parent application Ser. No. 07/23,035, as well as the following active ingredients which have been disclosed for use in similar dosage units in other co-pending, related applications: propranolol, triamterene, nifedipine, metoprolol, prazosin, methyldopa, clonidine, furosemide, verapamil, amiloride, digoxin, procainamide, hydralazine, fenoprofen, ibuprofen, diflunisal, lorazepam, indomethacin, clorazepate, haloperidol, perphenazine, trazodone, doxepin, propoxyphene, codeine, allopurinol, ergoloid mesylates, acetaminophen, methylprednisolone, methylphenidate, penicillin G, erythromycin, cefaclor, ephedrine, triprolidine, dexbrompheniramine, phenylpropanolamine.

The novel dosage units of the present invention provide unique advantages in terms of taste concealment for bitter or unpleasant orally active drugs, with a unique double layer of taste concealing materials that are inexpensive, and easy to obtain and manufacture in finished form. Moreover, the dosage units simultaneously overcome the difficulties in swallowing experienced by certain individuals in that they enable the ingestion of a plurality of tiny subdosage units which may readily be swallowed even by children or small animals, either directly or in a beverage or food medium. The admixture of a basic material with the copolymer resin in the outer coating of the subdosage pellets renders them far more non-tacky and easier to produce than the minipellets which I disclosed in U.S. Pat. No. 4,708,867.

The following examples provide detailed illustrations of the novel dosage units of the present invention. These examples are not intended, however, to limit or restrict the scope of the invention in any way, and should not be construed as providing methods, conditions, ingredients or starting materials which must be utilized exclusively to practice the present invention:

EXAMPLE 1

500 grams of nonpareil seeds, 30 to 35 mesh in size, are placed in a rotating coating pan. The seeds are wetted with a small amount of 5% povidone* solution in isopropanol. A small amount of chlorpheniramine powder is dusted onto the wetted nonpareil seeds. The wetting and dusting is repeated until 500 grams of chlorpheniramine are consumed. The drug-coated pellets are then dried in an oven. 700 grams of the dried drug-coated pellets are subsequently placed in a first six inch Worster fluid bed coater and spray coated with a slurry consisting of 5 grams of kaolin clay in 50 ml of a 2% povidone solution in isopropanol. The drug-coated pellets are again dried in an oven. Next, 15 grams of calcium carbonate suspended in solution of 10 grams of Eudragit E-100 copolymeric methacrylate resin in 100 ml of acetone is spray coated onto the pellets in a second fluid bed coater. The coating layer is than allowed to dry. The double coating substantially completely masks the taste of the chlorpheniramine coated on the pellet core.

*polyvinyl pyrrolidone

EXAMPLE 2

The coated pellets prepared according to Example 1 are divided into groups of 200 to 1000 pellets, with each group being packaged in a two-part openable standard gelatin capsule.

EXAMPLE 3

The coated pellets of Example 1 are divided into groups of 200 to 1000 pellets, with each group being packaged into single-dose, frangible receptacles consisting of breakable packets with a backing sheet of paper-coated aluminum foil material and a synthetic plastic container portion having a thin frangible zone or neck.

EXAMPLE 4

The capsule prepared according to Example 2 may be ingested by a human or animal patient, or is opened to enable the ingestion of the subdosage unit pellets contained therein. Likewise, the frangible packet of Example 3 is broken open at its frangible zone and the pellets contained therein ingested by a human or animal patient.

It has thus been shown that there are provided pharmaceutical dosage units for orally active pharmaceutical agents which achieve the various objects of the invention and which are well adapted to meet the conditions of practical use.

It will be understood that each of the elements described above, or two or more together, also may find a useful application in other types of constructions differing from the types described above.

While the invention has been described as embodied in a taste concealing pharmaceutical dosage unit, it is not intended to be limited to the details shown, since various modifications may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

I claim:

1. A pharmaceutical dosage unit comprising a plurality of subdosage units disposed within a container, each of said subdosage units being a pellet having an average diameter not greater than about 1 mm and including:
    (a) an inner core particle coated with an orally active pharmaceutical agent;
    (b) a first layer surrounding said core consisting of an inert clay or water-soluble polymer; and
    (c) a second layer surrounding said first layer comprising a mixture of from about 10% to about 90% by weight of a cationic copolymeric acrylate resin, and from about 10% to about 90% by weight of a basic compound selected from the group consisting of calcium carbonate, aluminum hydroxide and magnesium carbonate.

2. A dosage unit according to claim 1, which contains from about 50 to about 1000 subdosage units.

3. A dosage unit according to claim 2, which contains from about 200 to about 1000 subdosage units.

4. A dosage unit according to claim 1, wherein the aggregate quantity of the pharmaceutical agent contained in all of the subdosage units comprises a pharmaceutically effective dosage amount of said pharmaceutical agent.

5. A dosage unit according to claim 1, wherein said container is a frangible packet.

6. A dosage unit according to claim 1, wherein said container is an ingestible, openable capsule.

7. A dosage unit according to claim 1, wherein said core comprises a particle of a biologically acceptable salt, a sugar, or calcium phosphate.

8. A dosage unit according to claim 7, wherein said core is a nonpareil seed.

9. A dosage unit according to claim 1, wherein said pharmaceutical agent is adhered to the core by a binder material.

10. A dosage unit according to claim 9, wherein said binder material is selected from the group consisting of polyvinylpyrrolidone, methylcellulose, and pharmaceutically suitable gums.

11. A dosage unit according to claim 1, wherein said orally active pharmaceutical agent is selected from the group consisting of chlorpheniramine, propranolol, triamterene, nifedipine, metoprolol, prazosin, methyldopa, clonidine, furosemide, verapamil, amiloride, digoxin, procainamide, hydralazine, fenoprofen, ibuprofen, diflunisal, lorazepam, indomethacin, clorazepate, haloperidol, perphenazine, trazodone, doxepin, propoxyphene, codeine, allopurinol, ergoloid mesylates, acetaminophen, methylprednisolone, methylphenidate, penicillin G, erthromycin, cefaclor, ephedrine, triprolidine, dexbrompheniramine, and phenylpropanolamine.

12. A dosage unit according to claim 1, wherein said clay is kaolin clay.

13. A dosage unit according to claim 1, wherein said acrylate resin is based on methacrylate and neutral methacrylic acid ester copolymers.

14. A dosage unit according to claim 1, wherein said second layer comprises from about 40% to about 70% by weight of the acrylate resin, and from about 30% to about 60% by weight of the basic compound.

15. A dosage unit according to claim 11, wherein said pharmaceutical agent is chlorpheniramine.

* * * * *